US008822422B2

(12) United States Patent
Naoe et al.

(10) Patent No.: US 8,822,422 B2
(45) Date of Patent: Sep. 2, 2014

(54) ANTITUMOR AGENT

(75) Inventors: Yoshinori Naoe, Yokohama (JP); Takeshi Inoue, Osaka (JP); Yasuhiko Kano, Utsunomiya (JP)

(73) Assignee: Astellas Pharma Inc., Tokyo (JP)

(*) Notice: Subject to any disclaimer, the term of this patent is extended or adjusted under 35 U.S.C. 154(b) by 617 days.

(21) Appl. No.: 13/046,082

(22) Filed: Mar. 11, 2011

(65) Prior Publication Data
US 2011/0160295 A1 Jun. 30, 2011

Related U.S. Application Data

(63) Continuation of application No. 11/064,292, filed on Feb. 24, 2005, now Pat. No. 7,951,780.

(60) Provisional application No. 60/566,077, filed on Apr. 29, 2004.

(30) Foreign Application Priority Data

Feb. 25, 2004 (JP) ................. 2004-050520

(51) Int. Cl.
*A61K 38/12* (2006.01)
*A61P 35/00* (2006.01)
*C07K 7/50* (2006.01)
*A61K 31/122* (2006.01)
*A61K 45/06* (2006.01)
*A61K 31/337* (2006.01)

(52) U.S. Cl.
CPC ............ *A61K 31/337* (2013.01); *A61K 31/122* (2013.01); *A61K 45/06* (2013.01); *A61K 38/12* (2013.01)
USPC ........ 514/21.1; 530/317; 514/19.3; 424/155.1

(58) Field of Classification Search
None
See application file for complete search history.

(56) References Cited

U.S. PATENT DOCUMENTS

| 4,977,138 | A | 12/1990 | Okuhara et al. | |
|---|---|---|---|---|
| 6,252,058 | B1 * | 6/2001 | Thompson | 536/24.1 |
| 6,403,555 | B1 | 6/2002 | Skov | |
| 6,905,669 | B2 * | 6/2005 | DiMartino | 424/9.1 |
| 7,056,883 | B2 | 6/2006 | Ito et al. | |
| 7,056,884 | B2 | 6/2006 | Nakajima et al. | |
| 7,314,862 | B2 | 1/2008 | Naoe et al. | |
| 7,396,665 | B2 | 7/2008 | Ueda et al. | |
| 7,608,280 | B2 | 10/2009 | Ueda et al. | |
| 7,611,724 | B2 | 11/2009 | Ueda et al. | |
| 2004/0053820 | A1 | 3/2004 | Nakajima et al. | |
| 2005/0070467 | A1 | 3/2005 | Naoe et al. | |
| 2005/0187148 | A1 | 8/2005 | Naoe et al. | |
| 2005/0187149 | A1 | 8/2005 | Naoe et al. | |
| 2005/0191713 | A1 | 9/2005 | Sasakawa et al. | |
| 2006/0135413 | A1 | 6/2006 | Naoe et al. | |
| 2006/0223747 | A1 | 10/2006 | Ito et al. | |
| 2008/0233562 | A1 | 9/2008 | Sasakawa et al. | |
| 2009/0264343 | A1 | 10/2009 | Ueda et al. | |
| 2009/0264617 | A1 | 10/2009 | Ueda et al. | |

FOREIGN PATENT DOCUMENTS

| EP | 1 426 054 | 6/2004 |
|---|---|---|
| WO | WO 01/34131 | 5/2001 |
| WO | WO 02/06307 | 1/2002 |
| WO | WO 02/49501 A2 | 6/2002 |
| WO | WO 02/087335 A1 | 11/2002 |
| WO | WO 03/015810 | 3/2003 |
| WO | WO 03/020272 A1 | 3/2003 |
| WO | WO 03/024442 | 3/2003 |
| WO | WO 03/088954 | 10/2003 |
| WO | WO 2004/014386 A1 | 2/2004 |
| WO | WO 2004/064727 | 8/2004 |

OTHER PUBLICATIONS

Sandor, et al., 2000, British journal of Cancer, 83(6), 817-825 (listed in IDS dated Mar. 11, 2011).*
Chobanian, Anticancer Research 24: 539-546 (2004).*
Korean Office Action issued Oct. 25, 2011, in Patent Application No. 10-2006-7019173.
Yeul H. Kim, et al., "Paclitaxel, 5-Fluorouracil, and Cisplatin Combination Chemotherapy for the Treatment of Advanced Gastric Carcinoma", American Cancer Society, vol. 85, No. 2, Jan. 15, 1999, pp. 295-301.
Paul A. Marks, et al., "Histone Deacetylase Inhibitors: Inducers of Differentiation or Apoptosis of Transformed Cells", Journal of the National Cancer Institute, vol. 92, No. 15, Aug. 2, 2000, pp. 1210-1216.
Herbst, 2003, Cancer Treatment Reviews, 29, pp. 407-415.
Sandor, et al., 2000, British Journal of Cancer, 83(6), pp. 817-825.
Han, AAPS Pharmsci. (2000), 2(1), pp. 1-11.
Blagsosklonny, et al., The Journal of Clinical Investigation, 2000, 105, pp. 533-539.
Ettmayer, J. Med. Chem. (2004), 47(10), pp. 2393-2404.
Testa, Biochem. Pharm., (2004), 68, pp. 2097-2106.
Curtin, Expert Opin. Ther. Patents, 2002, 12(9), pp. 1375-1384.
Sreedharan, et al., "Pivanex, a Histone Deacetylase inhibitor, is synergistic with chemotherapy in inhibiting growth of human non-small cell lung cancer lines", Proceedings of the American Association for Cancer Research, vol. 44, No. 2d ed., XP-001154773, Jul. 2003, p. 742.

(Continued)

*Primary Examiner* — Satyanarayana R Gudibande
(74) *Attorney, Agent, or Firm* — Oblon, Spivak, McClelland, Maier & Neustadt, L.L.P.

(57) ABSTRACT

An antitumor agent containing, in combination, at least one kind of antitumor agent selected from the group consisting of an antitumor agent that forms a cross-link with DNA and shows an antitumor effect, an antimetabolite antitumor agent and a taxane antitumor agent, and a histone deacetylase inhibitor. According to the present invention, an antitumor agent causing reduced side effects and having a superior antitumor activity can be provided.

20 Claims, 4 Drawing Sheets

(56) References Cited

OTHER PUBLICATIONS

Furumai, et al., "FK228 (Depsipeptide) as a Natural Prodrug That Inhibits Class I Histone Deacetylases", Cancer Research 62, XP002381943, Sep. 1, 2002, pp. 4916-4921.
[Retrieved from] "http://en.wikipedia.org/wiki/Specific_activity", on Dec. 8, 2006.
[Retrieved from] "http://en.wikipedia.org/wiki/Surfactant", on Dec. 8, 2006.
Database Biosis Online, AN-PREV200400024248, XP-002342749, "Anti-Tumoral Efficacy of Four Different Histone Deacetylase Inhibitors on Hepatoma Cells in Vitro", 2003 (page Abstract No. T1786).
Nakajima, et al., "FR901228, A Potent Antitumor Antibiotic, Is a Novel Histone Deacetylase Inhibitor", Experimental Cell Research, vol. 241, 1998, pp. 126-133.
Li, et al., "Total Synthesis of the Antitumor Depsipeptide FR-901,228", J. Am. Chem. Soc., vol. 118, 1996, pp. 7237-7238.
Kano, et al, "Combined effects of histone deacetylase inhibitor FK228 and other anticancer agents—in vitro consideration", The Japanese Journal of Clinical Hematology, vol. 43, No. 8, Aug. 2002, p. 116 (with partial English translation).
Ueda, et al., "FR901228, A Novel Antitumor Bicyclic Depsipeptide Produced by *Chromobacterium violaceum* No. 968", The Journal of Antibiotics, vol. 47, No. 3, Mar. 1994, pp. 315-323.
Kosugi, et al., "In vivo Effects of a Histone Deacetylase Inhibitor, FK228, on Human Acute Promyelocytic Leukemia in NOD/Shi-scid/scid Mice", Jpn. J. Cancer Res. vol. 92, May 2001, pp. 529-536.
Piekarz, et al., "Inhibitor of histone deacetylation, depsipeptide (FR901228), in the treatment of peripheral and cutaneous T-cell lymphoma: a case report", Blood, vol. 98, No. 9, Nov. 1, 2001, pp. 2865-2868.
Sasakawa, et al., "Effects of FK228, a novel histone deacetylase inhibitor, on human lymphoma U-937 cells in vitro and in vivo", Biochemical Pharmacology, vol. 64, 2002, pp. 1079-1090.
Budillon, et al., "Growth arrest apoplosis and potentiation of 5-fluorouracil and Raltitrexed cytotoxic effect induced by Histone deacetylase inhibitor SAHA in Colorectal cancer cells", European Journal of Cancer, vol. 38, XP-004403521, Nov. 2002, p. S29.
Conway, et al., "Vincristine-and Cisplatin-induced Apoptosis in Human Retinoblastoma. Potentiation by Sodium Butyrate", European Journal of Cancer, vol. 34, No. 11, XP-004285125, Oct. 1998, pp. 1741-1748.
Sasakawa, et al., Cancer Leters, 2003, 195, pp. 161-168.
Office Action issued Jun. 14, 2011 in Japan Application No. 2006-526473.

\* cited by examiner (a) synergistic
(b) additive
(c) antagonistic

FK228 + cisplatin (simultaneous addition)

FK228 ⇒ cisplatin (continuous addition)

cisplatin ⇒ FK228 (continuous addition)

FK228 + 5-fluorouracil (simultaneous addition)

FK228 ⇒ 5-fluorouracil (continuous addition)

5-fluorouracil ⇒ FK228 (continuous addition)

paclitaxel ⇒ FK228 (continuous addition)

ANTITUMOR AGENT

CROSS REFERENCE TO RELATED APPLICATIONS

This application is a continuation of U.S. patent application Ser. No. 11/064,292, filed Feb. 24, 2005, the disclosure of which is incorporated herein by reference in its entirety. This application claims priority to Japanese Patent Application No. 2004-050520, filed Feb. 25, 2004, and U.S. Provisional Patent Application No. 60/566,077, filed Apr. 29, 2004, the disclosures of which are incorporated herein by reference in their entireties.

TECHNICAL FIELD OF THE INVENTION

The present invention relates to pharmaceutical compositions comprising, in combination, an antitumor agent selected from an antitumor agent that forms a cross-link with DNA and shows an antitumor effect, an antimetabolite antitumor agent and a taxane antitumor agent, and a pharmaceutical agent that remarkably enhances the antitumor effect and methods of using such agents.

BACKGROUND OF THE INVENTION

In the chemotherapy of tumors, particularly malignant tumors, in general, it is rare to achieve a desired antitumor effect by administration of a single antitumor agent, and in clinical situations, therefore, multiple drug therapy using two or more agents having different action mechanisms has been employed with the aim of increasing its effect. This combination therapy aims at alleviating side effects and enhancing antitumor action by combining antitumor agents having different action mechanisms, thereby to 1) decrease insensitive cell population, 2) prevent or delay development of drug resistance, 3) disperse toxicity by a combination of pharmaceutical agents with different toxicities and the like. However, random combinations of pharmaceutical agents with different action mechanisms for a combination therapy do not necessarily provide an antitumor effect-enhancing action or synergy.

It has been reported that histone deacetylase (HDAC) inhibitors induce high acetylation of histone and, as a result, induces transcription regulating activity on various genes, cell cycle inhibitory activity and apoptosis. Histone deacetylase inhibitors are also known as a potent anticancer agent (see JP-B-7-64872, Experimental Cell Research, US (1998), vol. 241, pp. 126-133).

For example, a compound represented by the formula (I)

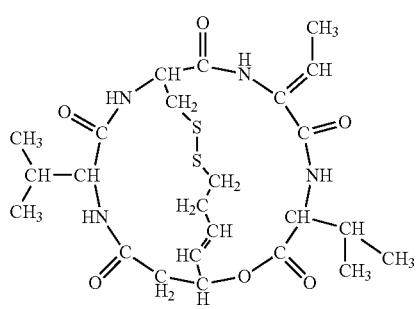

or a pharmaceutically acceptable salt thereof (hereinafter to be also referred to as compound A), particularly a stereoisomer represented by the formula (II)

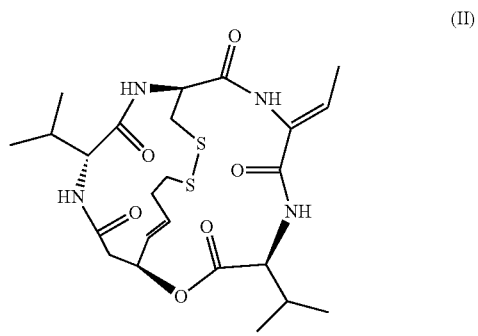 [SMILES: C/C=C1\NC(=O)[C@H]2CSSCC/C=C/[C@H](CC(=O)N[C@H](C(C)C)C(=O)N2)OC(=O)[C@H](C(C)C)NC1=O]

(hereinafter to be also referred to as FK228) or a pharmaceutically acceptable salt thereof are histone deacetylase inhibitors and reported to show a potent antitumor activity (see JP-B-7-64872 (corresponding to U.S. Pat. No. 4,977,138), Experimental Cell Research, US (1998), vol. 241, pp. 126-133).

However, a combined use of a histone deacetylase inhibitor and an antitumor agent that forms a cross-link with DNA and shows an antitumor effect, such as cisplatin and the like, an antimetabolite antitumor agent such as 5-fluorouracil and the like or a taxane antitumor agent, all of which are conventionally widely used as antitumor agents, as well as an effect afforded by the combined use have not been reported yet.

SUMMARY OF THE INVENTION

It is therefore an object of the present invention to provide an antitumor agent comprising, in combination, an antitumor agent selected from an antitumor agent that forms a cross-link with DNA and shows an antitumor effect, an antimetabolite antitumor agent and a taxane antitumor agent, and a pharmaceutical agent that remarkably enhances the antitumor effect, which reduces side effects and exhibits a superior antitumor activity.

As a result of intensive studies, the present inventors have found that a histone deacetylase inhibitor, particularly compound A known to have a potent histone deacetylase inhibitory activity, also remarkably enhances the antitumor effect of known antitumor agents: an antitumor agent that forms a cross-link with DNA and shows an antitumor effect, an antimetabolite antitumor agent and a taxane antitumor agent, which resulted in the completion of the present invention. Accordingly, the present invention provides the following.

[1] An antitumor agent and pharmaceutical compositions comprising, in combination, at least one kind of antitumor agent selected from the group consisting of an antitumor agent that forms a cross-link with DNA and shows an antitumor effect, an antimetabolite antitumor agent and a taxane antitumor agent, and a histone deacetylase inhibitor and methods of treating patients comprising administering such compositions and agents.

[2] The antitumor agent according to the above-mentioned [1], wherein the histone deacetylase inhibitor is a compound represented by the formula (I)

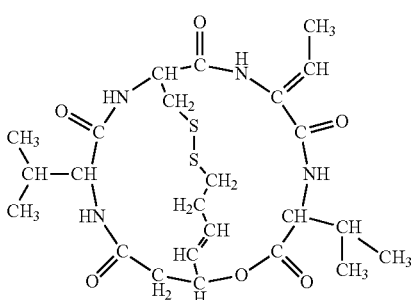

(I)

its reduction product, analogs, prodrugs or a pharmaceutically acceptable salt thereof.

[3] The antitumor agent according to the above-mentioned [2], wherein the antitumor agent that forms a cross-link with DNA and shows an antitumor effect is a platinum compound antitumor agent or an alkylating antitumor agent.

[4] The antitumor agent according to the above-mentioned [3], wherein the platinum compound antitumor agent is cisplatin.

[5] The antitumor agent according to the above-mentioned [2], wherein the antimetabolite antitumor agent is 5-fluorouracil.

[6] The antitumor agent according to the above-mentioned [2], wherein the taxane antitumor agent is at least one of paclitaxel and docetaxel.

[7] The antitumor agent according to any of the above-mentioned [1] to [6], which is an antitumor agent for lung cancer, malignant lymphoma, cancer of digestive organ, breast cancer, ovarian cancer, musculoskeletal sarcoma, bladder cancer, leukemia, kidney cancer or prostate cancer.

[8] An antitumor effect enhancer for at least one kind of antitumor agent selected from the group consisting of an antitumor agent that forms a cross-link with DNA and shows an antitumor effect, an antimetabolite antitumor agent and a taxane antitumor agent, which comprises a histone deacetylase inhibitor as an active ingredient, and methods of treating patients comprising administering such compositions and agents.

[9] The enhancer according to the above-mentioned [8], wherein the histone deacetylase inhibitor is a compound represented by the formula (I)

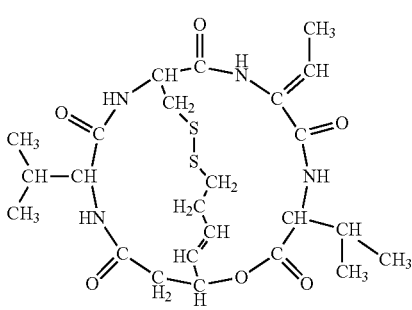

(I)

its reduction product, analogs, prodrugs or a pharmaceutically acceptable salt thereof.

[10] The enhancer according to the above-mentioned [9], wherein the antitumor agent that forms a cross-link with DNA and shows an antitumor effect is a platinum compound antitumor agent or an alkylating antitumor agent.

[11] The enhancer according to the above-mentioned [10], wherein the platinum compound antitumor agent is cisplatin.

[12] The enhancer according to the above-mentioned [9], wherein the antimetabolite antitumor agent is 5-fluorouracil.

[13] The enhancer according to the above-mentioned [9], wherein the taxane antitumor agent is at least one of paclitaxel and docetaxel.

[14] The enhancer according to any of the above-mentioned [8] to [13], which is an antitumor effect enhancer for lung cancer, malignant lymphoma, cancer of digestive organ, breast cancer, ovarian cancer, musculoskeletal sarcoma, bladder cancer, leukemia, kidney cancer or prostate cancer.

[15] A commercial package comprising a concomitant agent comprising at least one kind of antitumor agent selected from the group consisting of an antitumor agent that forms a cross-link with DNA and shows an antitumor effect, an antimetabolite antitumor agent and a taxane antitumor agent, and a written matter associated therewith, the written matter stating that the concomitant agent can or should be used as an antitumor agent with a histone deacetylase inhibitors.

[16] The commercial package according to the above-mentioned [15], wherein the histone deacetylase inhibitor is a compound represented by the formula (I)

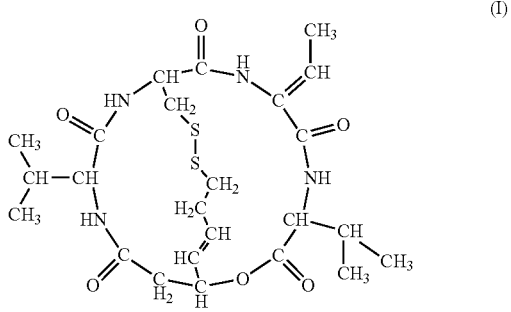 [SMILES: C/C=C1\NC(=O)C2CSSCC/C=C/C(CC(=O)NC(C(C)C)C(=O)N2)OC(=O)C(C(C)C)NC1=O]

(I)

its reduction product, analogs, prodrugs or a pharmaceutically acceptable salt thereof.

[17] The commercial package according to the above-mentioned [16], wherein the antitumor agent that forms a cross-link with DNA and shows an antitumor effect is a platinum compound antitumor agent or an alkylating antitumor agent.

[18] The commercial package according to the above-mentioned [17], wherein the platinum compound antitumor agent is cisplatin.

[19] The commercial package according to the above-mentioned [16], wherein the antimetabolite antitumor agent is 5-fluorouracil.

[20] The commercial package according to the above-mentioned [16], wherein the taxane antitumor agent is at least one of paclitaxel and docetaxel.

[21] A commercial package comprising a preparation containing a histone deacetylase inhibitor and a written matter associated therewith, the written matter stating that the preparation can or should be used for enhancing an antitumor effect of at least one kind of antitumor agent selected from the group consisting of an antitumor agent that forms a cross-link with DNA and shows an antitumor effect, an antimetabolite antitumor agent and a taxane antitumor agent.

[22] The commercial package according to the above-mentioned [21], wherein the histone deacetylase inhibitor is a compound represented by the formula (I)

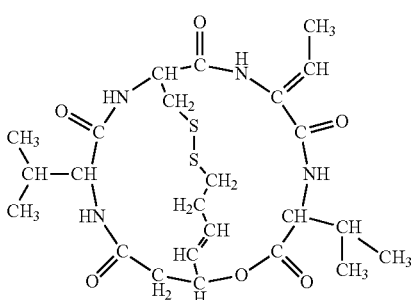

(I)

its reduction product, analogs, prodrugs or a pharmaceutically acceptable salt thereof.

[23] The commercial package according to the above-mentioned [22], wherein the antitumor agent that forms a cross-link with DNA and shows an antitumor effect is a platinum compound antitumor agent or an alkylating antitumor agent.

[24] The commercial package according to the above-mentioned [23], wherein the platinum compound antitumor agent is cisplatin.

[25] The commercial package according to the above-mentioned [22], wherein the antimetabolite antitumor agent is 5-fluorouracil.

[26] The commercial package according to the above-mentioned [22], wherein the taxane antitumor agent is at least one of paclitaxel and docetaxel.

DETAILED DESCRIPTION OF THE INVENTION

Figure 1:
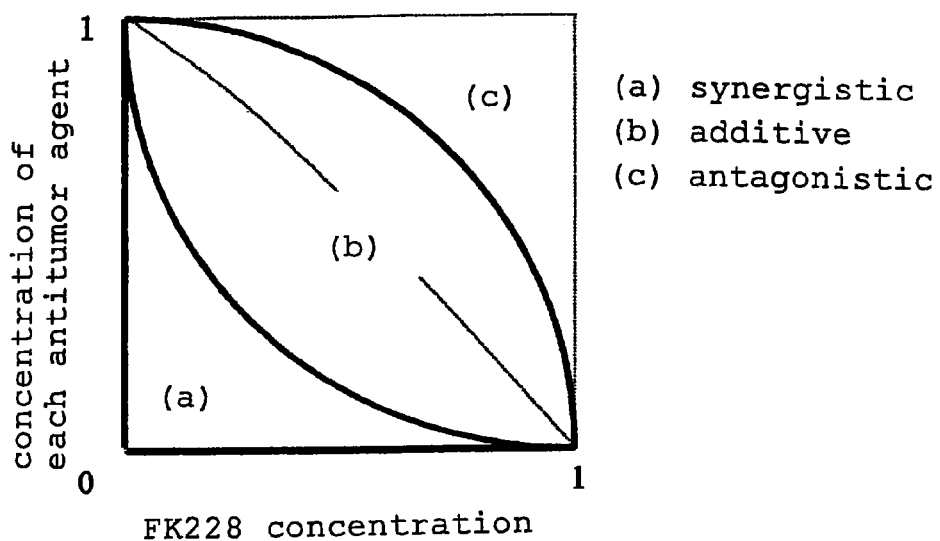
FIG. 1 is a graph showing the concept of the analysis.

Histone deacetylase inhibitors (particularly compound A and FK228) remarkably enhance the antitumor effect of an antitumor agent (particularly platinum compound antitumor agent or alkylating antitumor agent) that forms a cross-link with DNA and shows an antitumor effect, an antimetabolite antitumor agent or a taxane antitumor agent.

Therefore, the antitumor agent of the present invention comprising, in combination, at least one kind of antitumor agent selected from an antitumor agent that forms a cross-link with DNA and shows an antitumor effect, an antimetabolite antitumor agent and a taxane antitumor agent, and a histone deacetylase inhibitor affords a higher therapeutic effect against cancer at a smaller dose as compared to the administration of a single antitumor agent selected from an antitumor agent that forms a cross-link with DNA and shows an antitumor effect, an antimetabolite antitumor agent and a taxane antitumor agent, or a histone deacetylase inhibitor, and can suppress side effects to a lower level.

BEST MODE FOR EMBODYING THE INVENTION

The histone deacetylase inhibitor to be used in the present invention is a compound that binds to an active site of histone deacetylase competitively with substrates and/or shows an effect of decreasing the enzyme activity of histone deacetylase or otherwise inhibits enzyme activity and includes compounds known as histone deacetylase inhibitors. To be specific, the aforementioned compound A, a salt thereof and a derivative thereof (e.g., acetylated compound A, thiol form with reduced S—S bond etc. described in WO 02/06307) can be mentioned. Analogs of FK228 are described in U.S. Pat. No. 6,403,555. In addition, Trichostatin A, sodium butyrate, suberoylanilide hydroxamic acid (SAHA), MS-275, cyclic hydroxamic-acid-containing peptide, Apicidin, Trapoxin and the like are the compounds reported to have a histone deacetylase inhibitory activity. The histone deacetylase inhibitor may be one compound or a mixture of two or more compounds.

As the histone deacetylase inhibitor, compound A is preferably used. While compound A may have a stereoisomer (e.g., FK228) based on an asymmetric carbon atom or a double bond, such as an optically active form, a geometric isomer and the like, all these isomers and mixtures thereof are also encompassed in the scope of compound A.

Moreover, solvates (e.g., inclusion compounds (e.g., hydrates etc.)), anhydrous forms and other polymorphic forms or pharmaceutically acceptable salts of the compounds described herein are also encompassed in the scope of the present invention.

In the following description of the specification, unless particularly specified, a mere reference to compound A means a compound group including FK228 and a pharmaceutically acceptable salt, irrespective of the stereoisomerism.

The histone deacetylase inhibitors recited above include known and available substances. For example, FK228, which is one of the stereo isomers of compound A, can be obtained by culturing a strain belonging to the genus *Chromobacterium*, which is capable of producing FK228, under aerobic conditions, and harvesting the substance from its culture broth. As the strain belonging to the genus *Chromobacterium*, which is capable of producng FK228, for example, *Chromobacterium violaceum* WB968 (FERM BP-1968) can be mentioned. More specifically, FK228 can be obtained from a FK228-producing strain as described in JP-B-7-64872 (corresponding to U.S. Pat. No. 4,977,138). FK228 is preferably harvested from a strain belonging to the genus *Chromobacterium*, which is capable of producing FK228, because it can be obtained more easily. Synthetic or semi-synthetic FK228 is also advantageous in that further purification step is not necessary or the number of steps can be reduced. Similarly, compounds A other than FK228 can be also obtained by semi-synthesis or total synthesis by conventionally known methods. To be more specific, it can be produced according to the method reported by Khan W. Li, et al. (J. Am. Chem. Soc., Vol. 118, 7237-7238 (1996)).

Other histone deacetylase inhibitors, such as Tricostatin A, sodium butyrate, SAHA, MS-275, cyclic hydroxamic-acid-containing peptide, Apicidin, Trapoxin and the like are commercially available or can be prepared by known methods.

A pharmaceutically acceptable salt of compound A includes salts with a base or an acid addition salt such as salts with inorganic base (e.g., alkali metal salts such as sodium salt, potassium salt etc., alkaline earth metal salts such as calcium salt, magnesium salt etc., ammonium salt), salts with an organic base (e.g., organic amine salts such as triethylamine salt, diisopropylethylamine salt, pyridine salt, picoline salt, ethanolamine salt, triethanolamine salt, dicyclohexylamine salt, N,N'-dibenzylethylenediamine salt etc.), inorganic acid addition salts (e.g., hydrochloride, hydrobromide, sulfate, phosphate etc.), organic carboxylic acid or sulfonic acid addition salts (e.g., formate, acetate, trifluoroacetate, maleate, tartrate, fumarate, methanesulfonate, benzenesulfonate, toluenesulfonate etc.), salts with a basic or acidic amino acid (e.g., arginine, aspartic acid, glutamic acid etc.) and the like.

The antitumor agent that forms a cross-link with DNA and shows an antitumor effect to be used in the present invention may be any antitumor agent as long as it directly acts on DNA and forms a cross-link therewith to show an antitumor effect. Examples thereof include known platinum compound antitumor agents, known alkylating antitumor agent and the like. Specific examples thereof include cisplatin, carboplatin and the like for platinum compound antitumor agent, and cyclophosphamide, merphalan and the like for alkylating antitumor agent. The antitumor agent that forms a cross-link with DNA and shows an antitumor effect may be one kind of compound or two or more kinds of compounds in a mixture.

The antimetabolite antitumor agent to be used in the present invention may be any antimetabolite known as an antitumor agent. Specific examples include 5-fluorouracil, tegaful and the like. The antimetabolite antitumor agent may be one kind of compound or two or more kinds of compounds in a mixture.

The taxane antitumor agent used in the present invention includes various components or semisynthetic products thereof having, in the structure, a taxane skeleton isolated from *Taxusbrevifolia* or pure synthetic products having a taxane skeleton. Specifically, paclitaxel, docetaxel and the like can be mentioned. The taxane antitumor agent may be one kind of compound or two or more kinds of compounds in a mixture.

In the present invention, the histone deacetylase inhibitor (particularly compound A) remarkably enhances at least one kind of antitumor agent selected from an antitumor agent that forms a cross-link with DNA and shows an antitumor effect, an antimetabolite antitumor agent and a taxane antitumor agent. Therefore, the antitumor agent and the antitumor effect enhancer of the present invention are useful as therapeutic agents for cancerous diseases including blood cancer, solid tumor etc.; more specifically, lung cancer, malignant lymphoma (e.g., reticulosarcoma, lymphosarcoma, Hodgkin's disease etc.), cancer of digestive organ (e.g., gastric cancer, gallbladder cancer, bile duct cancer, pancreatic cancer, liver cancer, colon cancer, rectal cancer etc.), breast cancer, ovarian cancer, musculoskeletal sarcoma (e.g., osteosarcoma etc.), bladder cancer, leukemia (e.g., acute leukemia including blast crisis of chronic myeloid leukemia etc.), kidney cancer, prostate cancer and the like.

The at least one kind of antitumor agent selected from the group consisting of an antitumor agent that forms a cross-link with DNA and shows an antitumor effect, an antimetabolite antitumor agent and a taxane antitumor agent may be one kind of compound or two or more compounds administered separately or in a mixture.

In the present specification, unless particularly specified, by the "antitumor agent A" is meant "at least one kind of antitumor agent selected from the group consisting of an antitumor agent that forms a cross-link with DNA and shows an antitumor effect, an antimetabolite antitumor agent and a taxane antitumor agent".

The antitumor agent or pharmaceutical compositions of the present invention comprises a histone deacetylase inhibitor and an antitumor agent A in combination (i.e., concomitant agent) and may be any as long as it can comprise a histone deacetylase inhibitor and an antitumor agent A when in use for administration. The antitumor agent of the present invention may be a single preparation obtained by simultaneously preparing a histone deacetylase inhibitor and an antitumor agent A, or a combination of at least two preparations obtained by separately preparing a histone deacetylase inhibitor and an antitumor agent A.

The mode of administration is not particularly limited, and, for example, (1) administration of a composition containing a histone deacetylase inhibitor and an antitumor agent A, namely, administration of a single preparation, (2) simultaneous administration of two preparations by the same administration route, which are obtained by separately preparing a histone deacetylase inhibitor and an antitumor agent A, (3) staggered administration of two preparations by the same administration route, which are obtained by separately preparing a histone deacetylase inhibitor and an antitumor agent A (e.g., administration in the order of a histone deacetylase inhibitor and an antitumor agent A, or administration thereof in reverse order), (4) simultaneous administration of two preparations by different administration routes, which are obtained by separately preparing a histone deacetylase inhibitor and an antitumor agent A, (5) staggered administration of two preparations by different administration routes, which are obtained by separately preparing a histone deacetylase inhibitor and an antitumor agent A (e.g., administration in the order of a histone deacetylase inhibitor and an antitumor agent A, or administration thereof in reverse order) and the like can be mentioned.

The enhancer of the present invention contains a histone deacetylase inhibitor, and may be any as long as it can comprise a histone deacetylase inhibitor and an antitumor agent A in combination when in use for administration. Accordingly, as long as a histone deacetylase inhibitor is contained, the enhancer of the present invention may contain an antitumor agent A in a single preparation, and even if it does not contain an antitumor agent A, an antitumor agent A can be administered separately as a concomitant agent.

The administration mode is not particularly limited and, for example, (1) administration of the enhancer of the present invention containing a histone deacetylase inhibitor and an antitumor agent A in a single preparation, (2) simultaneous administration of the enhancer of the present invention and an antitumor agent A by the same administration route, (3) staggered administration of the enhancer of the present invention and an antitumor agent A by the same administration route (e.g., administration in the order of an antitumor agent A and the enhancer of the present invention, or administration thereof in reverse order), (4) simultaneous administration of the enhancer of the present invention and an antitumor agent A by different administration routes, (5) staggered administration of the enhancer of the present invention and an antitumor agent A by different administration routes (e.g., administration in the order of an antitumor agent A and the enhancer of the present invention, or administration thereof in reverse order) and the like can be mentioned.

In the present invention, the mixing ratio of the histone deacetylase inhibitor and the antitumor agent A can be, whether they are formulated into a single preparation or separate preparations, in the range of generally 1:100-100:1, preferably 1:10-10:1, by weight ratio.

When an antitumor agent A is to be formulated into a mixture of two or more kinds thereof, the mixing ratio is not particularly limited. When a mixture of an antitumor agent that forms a cross-link with DNA and shows an antitumor effect and an antimetabolite antitumor agent is to be made, the mixing ratio (weight ratio) is preferably in the range of 1:100-100:1; when a mixture of an antitumor agent that forms a cross-link with DNA and shows an antitumor effect and a taxane antitumor agent is to be made, the mixing ratio (weight ratio) is preferably in the range of 1:100-100:1; and when a mixture of an antimetabolite antitumor agent and a taxane antitumor agent is to be made, the mixing ratio (weight ratio) is preferably in the range of 1:100-100:1.

It is also preferable to administer the agent concomitantly with ATRA (all-trans-retinoic acid) (e.g., administration as a combined agent, simultaneous or separate administration as individual preparations), with the aim of enhancing the antitumor effect of the present invention.

The pharmaceutical compositions, antitumor agent A and/or histone deacetylase inhibitors of the present invention can be used in the form of a pharmaceutical preparation such as a solid, semisolid or liquid (tablet, pellet, troche, capsule, suppository, cream, ointment, aerosol, powder, liquid, emulsion, suspension, syrup, injection etc.) containing a histone deacetylase inhibitor and/or an antitumor agent A as active ingredient(s), which is suitable for transrectal, intranasal, pulmonary, vaginal, external (topical), oral or parenteral (including subcutaneous, implantation, intravenous and intramuscular) administration.

The antitumor effect enhancer of the present invention can be used in the form of a pharmaceutical preparation such as a solid, semisolid or liquid (tablet, pellet, troche, capsule, suppository, cream, ointment, aerosol, powder, liquid, emulsion, suspension, syrup, injection etc.) containing a histone deacetylase inhibitor as an active ingredient, which is suitable for transrectal, intranasal, pulmonary, vaginal, external (topical), oral or parenteral (including subcutaneous, implantation, intravenous and intramuscular) administration.

The antitumor agent and the antitumor effect enhancer of the present invention can be also produced by conventional methods using various organic or inorganic carriers conventionally used for forming pharmaceutical preparations, such as excipients (e.g., sucrose, starch, mannitol, sorbitol, lactose, glucose, cellulose, talc, calcium phosphate, calcium carbonate etc.), condensation agents (e.g., cellulose, methyl cellulose, hydroxypropyl cellulose, polypropylpyrrolidone, gelatin, gum arabic, polyethylene glycol, sucrose, starch etc.), disintegrants (e.g., starch, carboxymethyl cellulose, carboxymethyl cellulose calcium salt, hydroxypropylstarch, sodium carboxy methyl starch, sodium hydrogen carbonate, calcium phosphate, calcium citrate etc.), lubricants (e.g., magnesium stearate, earosil, talc, sodium lauryl sulfate etc.), corrigents (e.g., citric acid, menthol, glycine, orange powder etc.), preservatives (e.g., sodium benzoate, sodium hydrogen sulfite, methylparaben, propylparaben etc.), stabilizers (citric acid, sodium citrate, acetic acid etc.), suspension agents (e.g., methyl cellulose, polyvinyl pyrrolidone, aluminum stearate etc.), dispersants (e.g., hydroxypropylmethyl cellulose etc.), diluents (e.g., water etc.), wax base materials (e.g., cacao butter, polyethylene glycol, white petrolatum etc.) and the like.

The antitumor agent and the antitumor effect enhancer of the present invention can be administered to mammals inclusive of human in the form of the above-mentioned conventional pharmaceutical preparations without any particular limitation. In particular, intravenous, intramuscular or oral administration is preferable.

The dose in the present invention can be set to a lower level than that for separate administration of each of the histone deacetylase inhibitor and the antitumor agent A.

For example, the dose is appropriately determined according to various factors such as body weight and/or age of patients and/or severity of disease and administration route.

For example, when compound A is used as a histone deacetylase inhibitor and cisplatin is used as an antitumor agent A, the daily dose of compound A and cisplatin in combination in the case of an intravenous administration is generally 1-1000 mg, preferably 5-100 mg, more preferably 10-60 mg, per 1 $m^2$ of human body surface area, which is given for the treatment by continuous infusion. In this case, the daily dose of compound A is 0.1-100 mg, preferably 1-50 mg, more preferably 5-30 mg, in the amount of compound A, per 1 $m^2$ of human body surface area, and cisplatin is administered in the dose of [the aforementioned dose of a combination of compound A and cisplatin–the dose of compound A].

The present invention encompasses a commercial package comprising a concomitant agent comprising at least one kind of antitumor agent selected from the group consisting of an antitumor agent that forms a cross-link with DNA and shows an antitumor effect, an antimetabolite antitumor agent and a taxane antitumor agent and histone deacetylase inhibitor, and a written matter associated therewith, the written matter stating that the concomitant agent can or should be used as an antitumor agent; and a commercial package comprising a preparation containing a histone deacetylase inhibitor and a written matter associated therewith, the written matter stating that the preparation can or should be used for enhancing an antitumor effect of at least one kind of antitumor agent selected from the group consisting of an antitumor agent that forms a cross-link with DNA and shows an antitumor effect, an antimetabolite antitumor agent and a taxane antitumor agent.

EXAMPLES

Pharmacological test results showing the usefulness of the present invention are shown in the following.

Using FK228 as a histone deacetylase inhibitor, cisplatin (CDDP) as an antitumor agent that forms a cross-link with DNA and shows an antitumor effect, 5-fluorouracil (5-FU) as an antimetabolite antitumor agent and paclitaxel as a taxane antitumor agent, the effect of the combined use of the histone deacetylase inhibitor and each of the tumor agents was evaluated. For the evaluation test, human prostate cancer cell DU-145 (obtained from ATCC (AMERICAN TYPE CULTURE COLLECTION)) was cultured in 10% fetal bovine serum-containing Dulbecco's Modified Eagle Medium and applied to the test.

Experimental Example 1

Effect of Combined Use (Simultaneous Addition) of FK228 and Cisplatin

Prostate cancer cells ($6 \times 10^3$ cells/well) were cultured in a 96 well plate for 24 hr and FK228 (0.1 nM, 0.2 nM, 0.5 nM, 1 nM, 2 nM, 5 nM, 10 nM, 20 nM and 50 nM), cisplatin (50 nM, 100 nM, 200 nM, 500 nM, 1000 nM, 2000 nM and 5000 nM) or both pharmaceutical agents (simultaneous addition of the combination at the aforementioned concentrations) was/were added to achieve various concentrations. After culture for 24 hr, the cells were washed twice with 1% FBS (Fetal Bovine Serum)-containing PBS(−) (phosphate-buffered saline (calcium magnesium free)). The medium was changed to a drug-free medium and the cells were further cultured for 96 hr. FK228 was dissolved in ethanol and diluted with a medium before use, and cisplatin was diluted with a medium before use.

The antitumor activity after each treatment was evaluated by MTT assay. To be specific, 3-(4,5-dimethylthiazol-2-yl)-2,5-diphenyltetrazonium bromide (MTT) was dissolved in PBS at a concentration of 2.5 mg/mL, 20 μl thereof was added to each well and cultured for 4 hr. Formazan formed by living cells was dissolved by adding acidic isopropanol (100 μl) and the absorbance of each well was measured at a wavelength of 580 nm.

With the absorbance (OD) of non-treated cells as 100%, concentration-response curves of antitumor activity of a single pharmaceutical agent and a combination of pharmaceutical agents were drawn.

The effect of combined use of FK228 and cisplatin was evaluated by isobologram analysis according to the method of Steel et al. (Int. J. Radiat. Oncol. Biol. Phys., 5: 85-91, 1979). Namely, based on the concentration reaction curve of each single pharmaceutical agent, 80% growth inhibitory concentration ($IC_{80}$) by combined use was theoretically determined and shown by curves on a graph. The concentration of a pharmaceutical agent that achieved $IC_{80}$ in an actual combined use was plotted (see FIG. 1). When the plot was in an area (b) surrounded by the curves, an additive effect was determined to be present, when it was in an area (a) closer to the point of origin, a synergistic effect was determined to be present, and when it was in an area (c) farther from the point of origin, an antagonistic effect was determined to be present. The relative values were employed wherein $IC_{80}$ of a single agent was 1.

Figure 2:
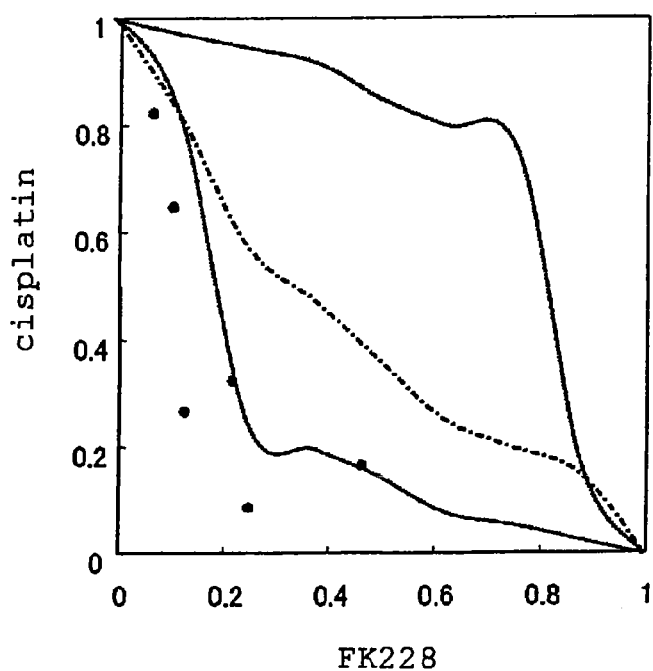
FIG. 2 is a graph showing the analysis of isobologram of combined use (simultaneous addition) of FK228 and cisplatin on DU-145 cells (Example 1).

The isobologram of Experimental Example 1 is shown in FIG. 2. As a result of the combined use (simultaneous addition) of FK228 and cisplatin, antitumor activity was remarkably enhanced.

Experimental Example 2

Effect of Combined Use (Continuous Addition) of FK228 and Cisplatin

Prostate cancer cells ($6 \times 10^3$ cells/well) were cultured in a 96 well plate for 24 hr and FK228 (0.1 nM, 0.2 nM, 0.5 nM, 1 nM, 2 nM, 5 nM, 10 nM, 20 nM and 50 nM) and cisplatin (50 nM, 100 nM, 200 nM, 500 nM, 1000 nM, 2000 nM and 5000 nM) were added to achieve various concentrations. After culture for 24 hr, the cells were washed twice with 1% FBS-containing PBS(−).

After washing, FK228 and cisplatin were added by continuous addition of both pharmaceutical agents in combination (added in the order of FK228⇒cisplatin or cisplatin⇒FK228 to achieve combination of each concentration). The mixture was further cultured for 24 hr and washed twice with 1% FBS-containing PBS(−). The medium was changed to a drug-free medium and the cells were further cultured for 72 hr. The effect of combined use was evaluated by a method similar to that in Experimental Example 1.

Figure 3:
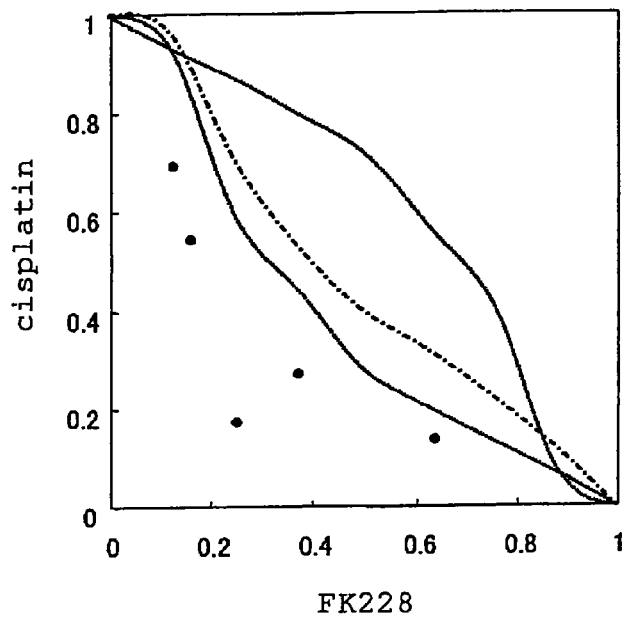
FIG. 3 is a graph showing the analysis of isobologram of combined use of FK228 and cisplatin (continuous addition in the order of FK228⇒cisplatin) on DU-145 cells (Example 2).
Figure 4:
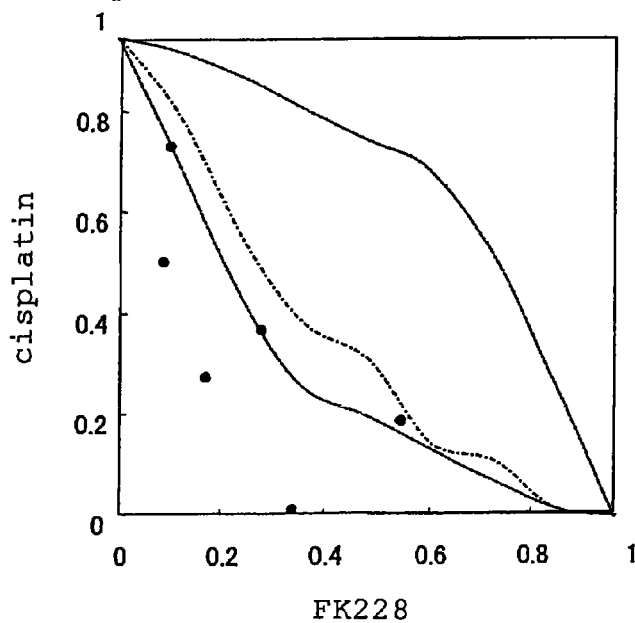
FIG. 4 is a graph showing the analysis of isobologram of combined use of FK228 and cisplatin (continuous addition in the order of cisplatin⇒FK228) on DU-145 cells (Example 2).

The isobologram of Experimental Example 2 is shown in FIG. 3 (addition order of FK228⇒cisplatin) and FIG. 4 (addition order of cisplatin⇒FK228). Remarkable enhancement of antitumor activity was afforded by the combined use (continuous addition) of FK228 and cisplatin in any order of addition (addition order of FK228⇒cisplatin or cisplatin⇒FK228).

Experimental Example 3

Effect of Combined Use (Simultaneous Addition) of FK228 and 5-fluorouracil

In the same manner as in Experimental Example 1 except that various concentrations of 5-fluorouracil (5 μM, 10 μM, 20 μM, 50 μM, 100 μM, 200 μM and 500 μM) were added instead of cisplatin, the effect of the combined use was evaluated. 5-Fluorouracil was diluted with a medium before addition.

Figure 5:
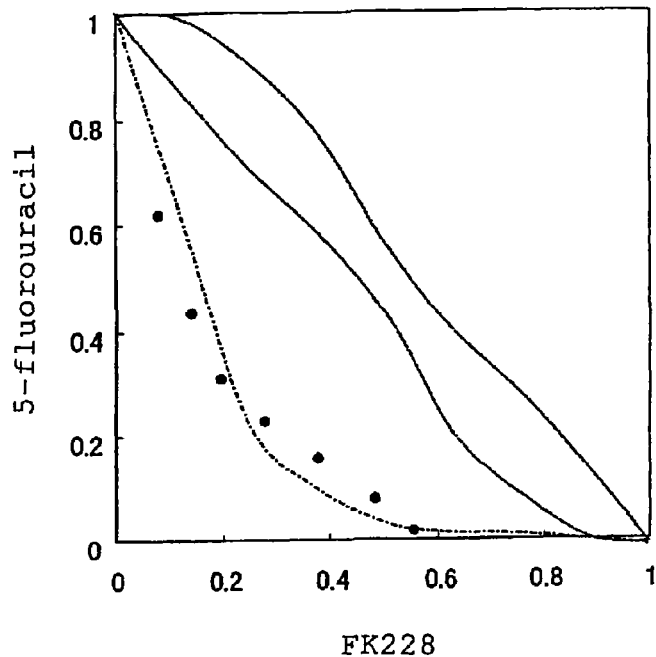
FIG. 5 is a graph showing the analysis of isobologram of combined use (simultaneous addition) of FK228 and 5-fluorouracil on DU-145 cells (Example 3).

The isobologram of Experimental Example 3 is shown in FIG. 5. The combined use (simultaneous addition) of FK228 and 5-fluorouracil enhanced the antitumor activity.

Experimental Example 4

Effect of Combined Use (Continuous Addition) of FK228 and 5-fluorouracil

In the same manner as in Experimental Example 2 except that various concentrations of 5-fluorouracil (5 μM, 10 μM, 20 μM, 50 μM, 100 μM, 200 μM and 500 μM for the addition order of 5-fluorouracil⇒FK228; and 100 μM, 200 μM, 500 μM, 1000 μM, 2000 μM, 5000 μM and 10000 μM for the addition order of FK228⇒5-fluorouracil) were added instead of cisplatin, the effect of the combined use was evaluated. 5-Fluorouracil was diluted with a medium before addition.

Figure 6:
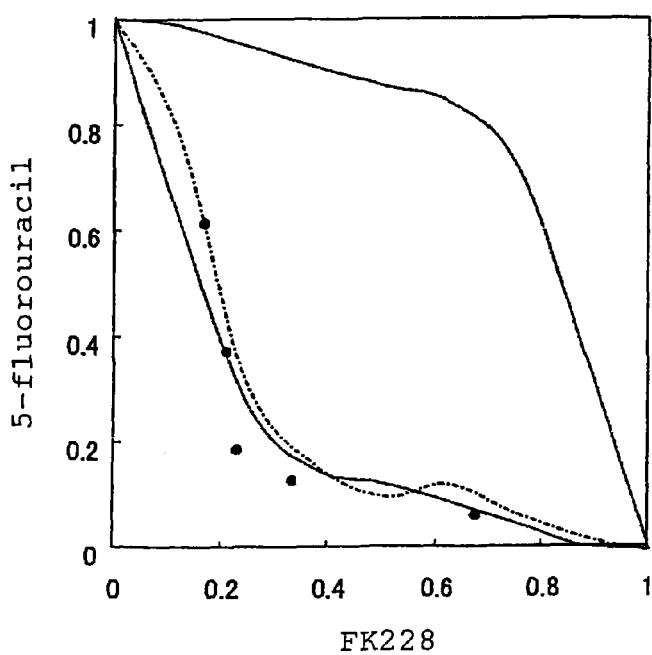
FIG. 6 is a graph showing the analysis of isobologram of combined use of FK228 and 5-fluorouracil (continuous addition in the order of FK228⇒5-fluorouracil) on DU-145 cells (Example 4).
Figure 7:
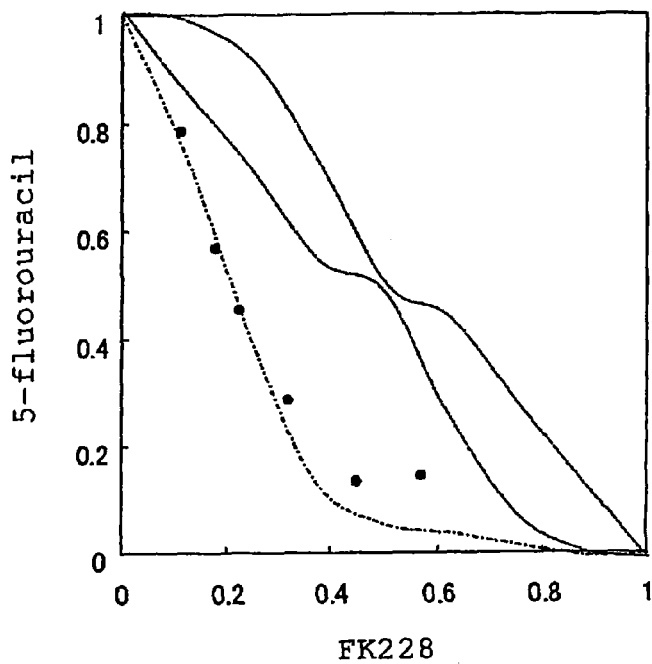
FIG. 7 is a graph showing the analysis of isobologram of combined use of FK228 and 5-fluorouracil (continuous addition in the order of 5-fluorouracil⇒FK228) on DU-145 cells (Example 4).

The isobologram of Experimental Example 4 is shown in FIG. 6 (addition order of FK228⇒5-fluorouracil) and FIG. 7 (addition order of 5-fluorouracil⇒FK228). The combined use (continuous addition) of FK228 and 5-fluorouracil in any order of addition (addition order of FK228⇒5-fluorouracil or 5-fluorouracil⇒FK228) enhanced the antitumor activity.

Experimental Example 5

Effect of Combined Use of FK228 and Paclitaxel (Continuous Addition in the Order of Paclitaxel⇒FK228)

In the same manner as in Experimental Example 2 except that various concentrations of paclitaxel (0.2 nM, 0.5 nM, 1 nM, 2 nM, 5 nM, 10 nM and 20 nM) were added in the order of paclitaxel⇒FK228 instead of cisplatin, the effect of the combined use was evaluated. Paclitaxel was dissolved in ethanol and diluted with a medium before addition.

Figure 8:
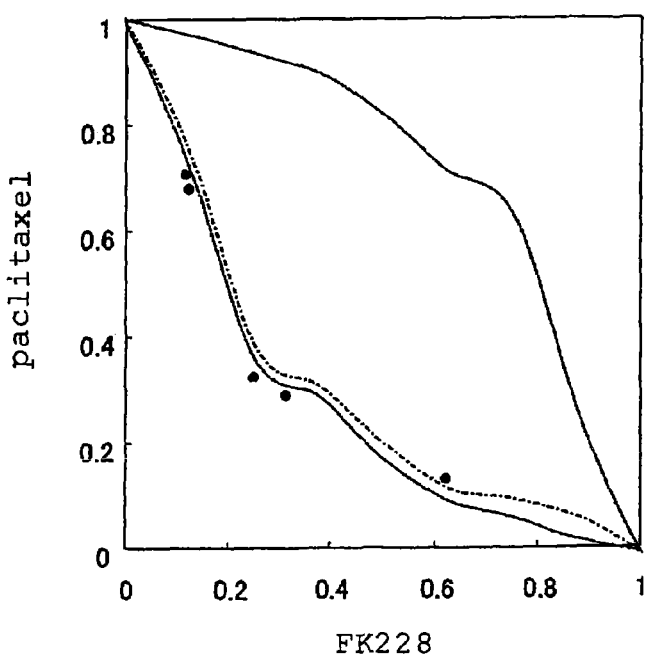
FIG. 8 is a graph showing the analysis of isobologram of combined use of FK228 and paclitaxel (continuous addition in the order of paclitaxel⇒FK228) on DU-145 cells (Example 5).

The isobologram of Experimental Example 5 is shown in FIG. 8. The combined use of FK228 and paclitaxel (continuous addition in the order of paclitaxel⇒FK228) enhanced the antitumor activity.

Formulation Example 1

| | |
|---|---|
| FK228 | 20 mg |
| ethanol | 20 ml |

FK228 (20 mg) is dissolved in and diluted with ethanol (20 ml) to give a preparation for injection.

Formulation Example 2

| | |
|---|---|
| FK228 | 20 mg |
| cisplatin | 100 mg |
| physiological saline | 100 ml |

FK228 (20 mg) and cisplatin (100 mg) are dissolved in and diluted with physiological saline (100 ml) to give a preparation for injection.

Formulation Example 3

| | |
|---|---|
| FK228 | 20 mg |
| 5-fluorouracil | 500 mg |
| ethanol | 100 ml |

FK228 (20 mg) and 5-fluorouracil (500 mg) are dissolved in and diluted with ethanol (100 ml) to give a preparation for injection.

Formulation Example 4

| | |
|---|---|
| FK228 | 20 mg |
| paclitaxel | 20 mg |
| ethanol | 40 ml |

FK228 (20 mg) and paclitaxel (20 mg) are dissolved in and diluted with ethanol (40 ml) to give a preparation for injection.

While this invention has been shown and described with references to preferred embodiments thereof, it will be understood by those skilled in the art that various changes in form and details may be made therein without departing from the scope of the invention encompassed by the appended claims.

All patents, patent publications and other publications identified or referenced herein are incorporated by reference in their entirety.

What is claimed is:

1. A method for chemotherapy of a tumor consisting of administering a compound of formula (I) and paclitaxel to a subject having prostate cancer;
wherein the compound of formula (I) is:

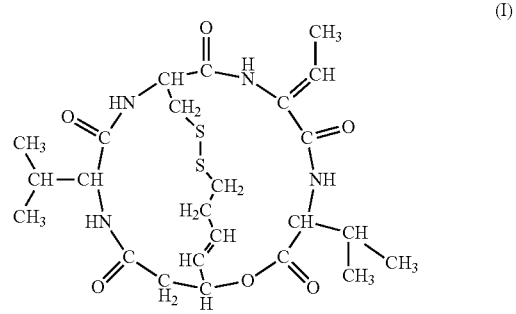 [SMILES: C/C=C1\NC(=O)C2CSSCC/C=C/C(CC(=O)NC(C(C)C)C(=O)N2)OC(=O)C(C(C)C)NC1=O]

(I)

or a pharmaceutically acceptable salt thereof.

2. The method of claim 1, wherein the compound of formula (I) is FK228 or a pharmaceutically acceptable salt thereof.

3. A method for treating cancer consisting of administering a compound of formula (I) and paclitaxel to a subject having prostate cancer;
wherein the compound of formula (I) is:

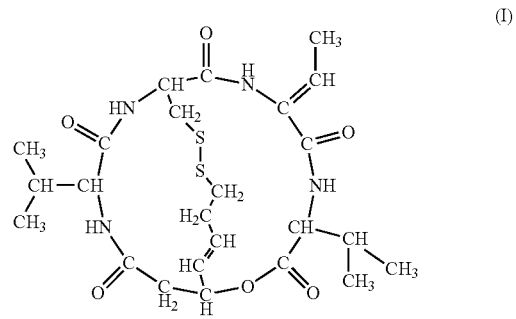 [SMILES: C/C=C1\NC(=O)C2CSSCC/C=C/C(CC(=O)NC(C(C)C)C(=O)N2)OC(=O)C(C(C)C)NC1=O]

(I)

or a pharmaceutically acceptable salt thereof.

4. The method of claim 3, wherein the compound of formula (I) is FK228 or a pharmaceutically acceptable salt thereof.

5. The method of claim 1, wherein the compound of formula (I) and paclitaxel are administered at a weight ratio (compound of formula (I):paclitaxel) of from 1:100 to 100:1.

6. The method of claim 1, wherein the compound of formula (I) and paclitaxel are administered at a weight ratio (compound of formula (I):paclitaxel) of from 1:10 to 10:1.

7. The method of claim 1, wherein at least one of the compound of formula (I) and paclitaxel is administered in the form of a solid pharmaceutical preparation.

8. The method of claim 7, wherein the pharmaceutical preparation is produced using at least one of an excipient, a condensation agent, a disintegrant, a lubricant, a corrigent, a preservative, a stabilizer, a suspension agent, a dispersant, a diluent, and a wax base material.

9. The method of claim 1, wherein at least one of the compound of formula (I) and paclitaxel is administered in the form of a semisolid pharmaceutical preparation.

10. The method of claim 9, wherein the pharmaceutical preparation is produced using at least one of an excipient, a condensation agent, a disintegrant, a lubricant, a corrigent, a preservative, a stabilizer, a suspension agent, a dispersant, a diluent, and a wax base material.

11. The method of claim 1, wherein at least one of the compound of formula (I) and paclitaxel is administered in the form of a liquid pharmaceutical preparation.

12. The method of claim 11, wherein the pharmaceutical preparation is produced using at least one of an excipient, a condensation agent, a disintegrant, a lubricant, a corrigent, a preservative, a stabilizer, a suspension agent, a dispersant, a diluent, and a wax base material.

13. The method of claim 3, wherein the compound of formula (I) and paclitaxel are administered at a weight ratio (compound of formula (I):paclitaxel) of from 1:100 to 100:1.

14. The method of claim 3, wherein the compound of formula (I) and paclitaxel are administered at a weight ratio (compound of formula (I):paclitaxel) of from 1:10 to 10:1.

15. The method of claim 3, wherein at least one of the compound of formula (I) and paclitaxel is administered in the form of a solid pharmaceutical preparation.

16. The method of claim 15, wherein the pharmaceutical preparation is produced using at least one of an excipient, a condensation agent, a disintegrant, a lubricant, a corrigent, a preservative, a stabilizer, a suspension agent, a dispersant, a diluent, and a wax base material.

17. The method of claim 3, wherein at least one of the compound of formula (I) and paclitaxel is administered in the form of a semisolid pharmaceutical preparation.

18. The method of claim 17, wherein the pharmaceutical preparation is produced using at least one of an excipient, a condensation agent, a disintegrant, a lubricant, a corrigent, a preservative, a stabilizer, a suspension agent, a dispersant, a diluent, and a wax base material.

19. The method of claim 3, wherein at least one of the compound of formula (I) and paclitaxel is administered in the form of a liquid pharmaceutical preparation.

20. The method of claim 19, wherein the pharmaceutical preparation is produced using at least one of an excipient, a condensation agent, a disintegrant, a lubricant, a corrigent, a preservative, a stabilizer, a suspension agent, a dispersant, a diluent, and a wax base material.

* * * * *